United States Patent [19]

Ward

[11] Patent Number: 5,275,720
[45] Date of Patent: Jan. 4, 1994

[54] GASOLINE HYDROCRACKING CATALYST AND PROCESS

[75] Inventor: John W. Ward, Yorba Linda, Calif.

[73] Assignee: Union Oil Company of California, Los Angeles, Calif.

[21] Appl. No.: 621,362

[22] Filed: Nov. 30, 1990

[51] Int. Cl.$^5$ .............................................. C10G 47/20
[52] U.S. Cl. ..................... 208/111; 208/46; 208/108
[58] Field of Search ............................ 208/111, 111

[56] References Cited

U.S. PATENT DOCUMENTS

| Re. 28,341 | 2/1975 | Wadlinger et al. | 208/120 |
|---|---|---|---|
| 3,923,641 | 12/1975 | Morrison | 208/111 |
| 4,477,336 | 10/1984 | Scherzer | 208/120 |
| 4,486,296 | 12/1984 | Oleck et al. | 208/111 |
| 4,503,023 | 3/1985 | Breck et al. | 423/328 |
| 4,534,853 | 8/1985 | Long et al. | 208/120 |
| 4,568,655 | 2/1986 | Oleck et al. | 502/66 |
| 4,588,496 | 5/1986 | Scherzer | 208/120 |
| 4,601,993 | 7/1986 | Chu et al. | 502/66 |
| 4,612,108 | 9/1986 | Angevine et al. | 208/111 |
| 4,676,887 | 6/1987 | Fischer et al. | 208/61 |
| 4,711,770 | 12/1987 | Skeels et al. | 423/528 |
| 4,735,928 | 4/1988 | Best et al. | 502/63 |
| 4,740,292 | 4/1988 | Chen et al. | 208/120 |
| 4,756,822 | 7/1988 | Chen et al. | 208/111 |
| 4,795,549 | 1/1989 | Coughlin et al. | 208/139 |
| 4,812,223 | 3/1989 | Hickey, Jr. et al. | 208/111 |
| 4,816,538 | 3/1989 | Abdo | 502/66 |
| 4,837,396 | 6/1989 | Herbst et al. | 502/67 |
| 4,857,169 | 8/1989 | Abdo | 208/59 |
| 4,867,861 | 9/1989 | Abdo et al. | 208/27 |
| 4,891,458 | 1/1990 | Innes et al. | 585/323 |
| 4,897,178 | 1/1990 | Best et al. | 208/111 |
| 4,898,846 | 2/1990 | Edwards et al. | 502/67 |
| 4,911,823 | 3/1990 | Chen et al. | 208/67 |
| 4,916,096 | 4/1990 | Hoek et al. | 502/66 |
| 4,985,384 | 1/1991 | Gilson | 502/61 |
| 5,037,531 | 8/1991 | Bundens et al. | 207/111 |
| 5,100,535 | 3/1992 | Chen et al. | 208/111 |

FOREIGN PATENT DOCUMENTS

| 0028938 | 5/1981 | European Pat. Off. | C10G 47/06 |
|---|---|---|---|
| 0243629 | 11/1987 | European Pat. Off. | C10G 11/05 |

Primary Examiner—Helane Myers
Attorney, Agent, or Firm—Yale S. Finkle; Gregory F. Wirzbicki

[57] ABSTRACT

A catalyst for use in acid catalyzed chemical conversion processes such as hydrocarbon conversion processes comprises zeolite beta and a dealuminated Y zeolite having an overall silica-to-alumina mole ratio greater than 6.0, preferably LZ-210 zeolite. A preferred catalyst contains nickel and molybdenum hydrogenation components in addition to the zeolite beta and the LZ-210 zeolite and, when used in gasoline hydrocracking, is found to be more active and selective for both light and heavy gasoline than a commercially available gasoline hydrocracking catalyst containing nickel and molybdenum hydrogenation components and a single steam-stabilized Y zeolite.

46 Claims, No Drawings

5,275,720

GASOLINE HYDROCRACKING CATALYST AND PROCESS

BACKGROUND OF THE INVENTION

This invention relates to acid catalyzed chemical conversion processes, such as hydrocarbon conversion processes, and to the catalysts used in such processes. The invention is particularly concerned with a catalyst containing a combination of two zeolites and the use of the catalyst in hydrocracking to selectively produce gasoline.

Petroleum refiners often produce desirable products, such as gasoline and turbine fuel, by catalytically hydrocracking high boiling hydrocarbons into product hydrocarbons of lower average molecular weight and boiling point. Hydrocracking is generally accomplished by contacting, in an appropriate reactor vessel, a gas oil or other hydrocarbon feedstock with a suitable hydrocracking catalyst under appropriate conditions, including an elevated temperature and an elevated pressure and the presence of hydrogen, such that a hydrocarbon product is obtained containing a substantial portion of a desired product boiling in a specified range, as for example, a gasoline boiling in the range of 185° to 420° F.

Oftentimes, hydrocracking is performed in conjunction with hydrotreating, usually by a method referred to as "integral operation." In this process, the hydrocarbon feedstock, usually a gas oil containing a substantial proportion of components boiling above a desired end point, as for example, 420° F. in the case of certain gasolines, is introduced into a catalytic hydrotreating zone wherein, in the presence of a suitable catalyst, such as a zeolite- or sieve-free particulate catalyst comprising a Group VIII metal component and a Group VIB metal component on a porous, inorganic refractory oxide support most often composed of alumina, and under suitable conditions, including an elevated temperature (e.g., 400° to 1000° F.) and an elevated pressure (e.g., 100 to 5000 p.s.i.a.) and with hydrogen as a reactant, the organonitrogen components and the organosulfur components contained in the feedstock are converted to ammonia and hydrogen sulfide, respectively. Subsequently, the entire effluent removed from the hydrotreating zone is treated in a hydrocracking zone maintained under suitable conditions of elevated temperature, pressure, and hydrogen partial pressure, and containing a suitable hydrocracking catalyst, such that a substantial conversion of high boiling feed components to product components boiling below the desired end point is obtained. Usually, the hydrotreating and hydrocracking zones in integral operation are maintained in separate reactor vessels, but, on occasion, it may be advantageous to employ a single, downflow reactor vessel containing an upper bed of hydrotreating catalyst particles and a lower bed of hydrocracking particles. Examples of integral operation may be found in U.S. Pat. Nos. 3,132,087, 3,159,564, 3,655,551, and 4,040,944, all of which are herein incorporated by reference in their entireties.

In some integral operation refining processes, and especially those dssigned to produce gasoline from the heavier gas oils, a relatively high proportion of the product hydrocarbons obtained from integral operation will have a boiling point above the desired end point. For example, in the production of a gasoline product boiling in the $C_4$ to 420° F. range from a gas oil boiling entirely above 570° F., it may often be the case that as much as 30 to 60 percent by volume of the products obtained from integral operation boil above 420° F. To convert these high boiling components to hydrocarbon components boiling below 420° F., the petroleum refiner separates the 420° F.+ high boiling components from the other products obtained in integral operation, usually after first removing ammonia by a water washing operation, a hydrogen-containing recycle gas by high pressure separation, and an $H_2S$-containing, $C_1$ to $C_3$ low BTU gas by low pressure separation. This 420° F.+ bottom fraction is then subjected to further hydrocracking, either by recycle to the hydrocracking reactor in single stage operation or by introduction into a second hydrocracking zone wherein yet more conversion to the desired $C_4$ to 420° F. product takes place.

In the foregoing two stage process, the two hydrocracking reaction zones often contain hydrocracking catalysts of the same composition. One catalyst suitable for such use is disclosed as Catalyst A in Example 16 of U.S. Pat. Nos. 3,897,327 and 3,929,672, both of which are herein incorporated by reference in their entireties, which catalyst is comprised of a palladium-exchanged steam stabilized Y zeolite hydrocracking component. But although the catalysts used in the two hydrocracking reaction zones may have the same composition and the same catalytic properties, the hydrocracking conditions required in the second hydrocracking reaction zone are less severe than those required in the first. The reason for this is that ammonia is not present in the second hydrocracking reaction zone (due to water washing) whereas a significant amount of ammonia is present in the first hydrocracking zone. To account for the difference in operating conditions, it is believed that ammonia neutralizes or otherwise interferes with the acidity of the zeolite in the catalyst of the first reaction zone, thereby forcing the refiner to employ relatively severe conditions for operation, as for example, increased temperature. On the other hand, in the ammonia-deficient atmosphere of the second hydrocracking reaction zone, high conversions to the desired product are obtainable under relatively moderate conditions, often with an operating temperature about 100° to 210° F. lower than that required in the first hydrocracking reaction zone.

Further decription of two-stage hydrocracking operations may be found in U.S. Pat. Nos. 4,429,053 and 4,857,169 herein incorporated by reference in their entireties, which patents provide a process flow sheet for a typical two-stage hydrocracking process.

Although there exist several types of commercial hydrocracking catalysts which can be used effectively in either the first, second or both stages of the above-discussed two-stage hydrocracking process, there is always a demand for new catalysts with superior overall activity, selectivity and stability for gasoline hydrocracking.

SUMMARY OF THE INVENTION

In accordance with the invention, it has now been found that catalysts containing zeolite beta and a dealuminated Y zeolite having an overall silica-to-alumina mole ratio greater than 6.0 are especially useful in the acid catalyzed chemical conversion of feedstocks containing organic compounds into reaction products, particularly in the acid catalyzed conversion of hydrocarbons. It has been further found that, when such catalysts also contain at least one hydrogenation component, such as one or more Group VIB or Group VIII metal components, they are particularly suited for use in hydrocracking. Preferred catalysts of the invention contain a Group VIB metal component, a Group VIII non-noble metal component, zeolite beta, the dealuminated Y zeolite known as LZ-210 zeolite and a porous, inorganic refractory oxide binder.

Preliminary tests indicate that the catalysts of the invention, when used in hydrocracking to produce gasoline, have a higher activity and selectivity, both for first stage (in the presence of NH$_3$) and second stage (in the substantial absence of NH$_3$) hydrocracking as compared to a hydrocracking catalyst now commercially available for use in gasoline hydrocracking processes. Thus, the catalyst and process of the invention appear to be significant improvements in the art of gasoline hydrocracking.

DETAILED DESCRIPTION OF THE INVENTION

The present invention is directed to a novel catalyst and novel acid catalyzed chemical conversion processes employing such catalysss to promote the desired reactions. The present invention is particularly directed to hydrocracking catalysts, and hydrocracking processes employing such catalysts, comprising a hydrogenation component(s), zeolite beta and a dealuminated Y zeolite having an overall silica-to-alumina mole ratio greater than 6.0.

Zeolite beta is a crystalline aluminosilicate zeolite whose composition and X-ray powder diffraction analysis are disclosed in U.S. Pat. No. 28,341, herein incorporated by reference in its entirety. This zeolite is a large pore zeolite having a pore size above 7.0 angstroms and a Constraint Index below 2, preferably between 0.6 and 1.0. The Constraint Index of a zeolite is a convenient measure of the extent to which a zeolite provides access to molecules of varying sizes to its internal structure. Zeolites which provide a highly restricted access to and egress from its internal structure have a high value for the Constraint Index, and zeolites of this kind usually have pores of small size. On the other hand, zeolites which provide relatively free access to the internal zeolite structure have a low value for the Constraint Index. The method by which Constraint Index is determined is described fully in U.S. Pat. No. 4,0167,218, the disclosure of which is hereby incorporated by reference in its entirety.

Zeolite beta is prepared, in general, as an aluminosilicate zeolite having a silica-to-alumina mole ratio (SiO$_2$:Al$_2$O$_3$) of at least 10 up to about 100, but preferably no more than about 40, and most preferably in the range of 20 to 30. It may also be prepared in yet higher silica-to-alumina mole ratios, e.g., 500:1 or more, and although such materials may have little or no zeolitic properties, it is to be understood that, in the present invention, the term "zeolite beta" is meant to encompass such materials. The preferred zeolite betas have a crystal size of about 0.1 to 0.7 um, a surface area of about 500 to 800, preferably 650 to 750, and most preferably 700 to 750 m$^2$/gm, and a cyclohexane adsorption capacity of about 15 to 25 gm/100 gm.

As initially prepared, zeolite beta is usually in the alkali metal form with an organic templating agent. In this form, the zeolite has little if any catalytic activity for promoting acid catalyzed conversion reactions, e.g., cracking reactions. Accordingly, the zeolite is generally converted to more active forms, generally by base exchange with ammonium cations to substantially reduce the alkali metal content, followed by calcination to decompose the organic templating agent and convert the zeolite to the hydrogen form. Alternatively, the zeolite may be calcined first to drive off the templating agent, followed by ammonium ion exchange and another calcination to convert the zeolite to the hydrogen form. For zeolite betas initially prepared in the sodium form, the preferred sodium content upon conversion to an active form is below 1.0 percent by anhydrous weight, frequently below about 0.5 percent by anhydrous weight, calculated as Na$_2$O.

Publications which further discuss the properties of zeolite beta include U.S. Pat. Nos. 3,923,641, 4,676,887, 4,812,223, 4,486,296, 4,601,993 and 4,612,108, all of which are herein incorporated by reference in their entireties.

Also included in the catalyst of the invention is a dealuminated Y zeolite having an overall silica-to-alumina mole ratio greater than 6.0, preferably between about 6.1 and 20.0, and most preferably between about 8.0 and 15.0. The dealuminated Y zeolite is prepared by chemically dealuminating a crystalline aluminosilicate zeolite of the Y-type having a silica-to-alumina mole ratio below about 6.0. Normally, the Y zeolite starting material will be in the sodium form, containing between about 10 and about 14 weight percent sodium calculated as Na$_2$O. U.S. Pat. No. 3,130,007, the disclosure of which is hereby incorporated by reference in its entirety, describes Y-type zeolites having a silica-to-alumina mole ratio between about 3.0 and about 6.0, with a typical Y zeolite having a silica-to-alumina mole ratio of about 5.0.

Since the dealuminated Y zeolite used in the catalyst is usually prepared from a Y zeolite starting material, it will have the essential X-ray powder diffraction pattern of Y zeolite. It will be understood, however, that in converting a Y zeolite starting material to a dealuminated zeolite useful in the present invention, the resulting dealuminated zeolite may not have exactly the same X-ray powder diffraction pattern for Y zeolites as is disclosed in U.S. Pat. No. 3,130,007. The d-spacings may be shifted somewhat due to cation exchanges, calcinations, shrinkage in the unit cell size due to the increase in the silica-to-alumina mole ratio, etc. The essential crystal structure of Y zeolite will, however, be retained so that the essential X-ray powder diffraction pattern of the dealuminated zeolite used in the catalyst will be consistent with that of either Y zeolite itself or a Y zeolite of reduced unit cell size. Normally, the unit cell size for the dealuminated Y zeolite used in the catalyst will be between about 24.40 and 24.65 angstroms.

The dealuminated Y zeolites used in the catalyst may be prepared by any conventional method of dealumination as long as the overall silica-to-alumina mole ratio, as opposed to the framework silica-to-alumina mole ratio, of the Y zeolite starting material is increased in value from below about 6.0 to above about 6.0. There are three general methods for preparing dealuminated Y zeolites. One of these methods, hydrothermal treatment, increases the framework silica-to-alumina mole ratio but not the overall silica-to alumina mole ratio. The other two methods, chemical treatment and a combination of hydrothermal and chemical treatment, increase both the overall and framework silica-to-alumina mole ratio. Hydrothermal dealumination involves calcination of the ammonium or hydrogen form of the Y zeolite starting material at relatively high temperatures, typically above about 900° F., in the presence of steam. This treatment, which is typically used to prepare steam-stabilized and ultrastable Y zeolites, results in the expulsion of tetrahedral aluminum from framework into nonframework positions and resultant increase in framework silica-to-alumina mole ratio, but normally does not remove the aluminum from the zeolite and therefore does not increase the overall silica-to-alumina mole ratio of the starting Y zeolite. Thus, chemical treatment and a combination of hydrothermal and chemical treatment are the methods that are typically used to prepare the dealuminated Y zeolites that comprise the catalysts of the invention.

Chemical dealumination is achieved by reacting the starting Y zeolite with a suitable reagent in an aqueous or nonaqueous solution or by reacting the zeolite with a reagent in the vapor phase at a high temperature. Dealumination in solution is normally accomplished by reacting the zeolite with solutions of acids, salts, or chelating agents, and, in some cases, may involve the insertion of silicon from the solutions into the framework structure to replace aluminum removed therefrom. The combination of thermal and chemical dealumination is typically a two-step method used to obtain a higher degree of dealumination. The mechanism during the thermal treatment step is similar to the one described above for thermal dealumination. High temperatures and steam enhance the expulsion of aluminum from the framework. The chemical treatment then involves the solubilization primarily of nonframework aluminum generated during the thermal treatment step. The nonframework aluminum can be in the form of cationic and neutral species, the amount and composition of which depend upon the conditions of the thermal treatment. Specific methods of thermal and chemical dealumination are described in detail in the article entitled "The Preparation and Characterization of Aluminum Deficient Zeolites" appearing in *Catalytic Materials: Relationship Between Structure and Reactivity*, ACS Symposium Series 248, 1984, and in U.S. Pat. No. 4,897,178 the disclosures of which article and patent are hereby incorporated by reference in their entireties.

The dealuminated Y zeolite used in the catalyst of the invention is a large pore zeolite having an effective pore size greater than 7.0 angstroms, and in contrast to non-dealuminated Y zeolites, may contain some pores having a size between 20 and 60 angstroms. The pores are typically defined by unpuckered 12-membered rings of oxygen atoms. Since some of the pores of the dealuminated Y zeolite are relatively large, the zeolite provides molecules relatively free access to its internal structure. Thus, the dealuminated Y zeolite will typically have a low Constraint Index, typically below 1.0, preferably below 0.75, and usually below about 0.5.

The preferred dealuminated Y zeolites for use in the catalyst of the invention are a group of zeolites known as LZ-210 zeolites, zeolitic aluminosilicate molecular sieves available from UOP. These zeolites are described in detail in U.S. Pat. Nos. 4,503,023 and 4,711,770, the disclosures of which are hereby incorporated by reference in their entireties. The preferred LZ-210 zeolites for use in the invention have a chemical composition expressed in terms of oxide mole ratios in the anhydrous state of $$(0.85-1.1)M_{2/n}O:Al_2O_3:xSiO_2$$

wherein "M" is a cation having the valence "n" and "x" is a value between 6 and about 20, preferably between 6 and about 15, more preferably between about 8 and about 15, and most preferably from about 9 to 13. These LZ-210 zeolites have extraneous silicon atoms in their crystal lattice in the form of $SiO_4$ tetrahedra, preferably in an average amount of at least 1.0 per 10,000 cubic angstroms and typically have an X-ray powder diffraction pattern having at least the d-spacings set forth below:

TABLE 1

| d(Angstroms) | Intensity |
|---|---|
| 14.17–13.97 | very strong |
| 8.68–8.55 | medium |
| 7.40–7.30 | medium |
| 5.63–5.55 | strong |
| 4.72–4.66 | medium |
| 4.34–4.28 | medium |
| 3.74–3.69 | strong |
| 3.28–3.23 | strong |
| 2.83–2.79 | strong |

LZ-210 zeolites are conveniently prepared from a Y zeolite starting material in silica-to-alumina mole ratios between about 6.0 and about 20, although higher ratios are possible. Typically, the unit cell size is at or below 24.63 angstroms and will normally range between about 24.40 and about 24.63 angstroms, preferably between about 24.47 and 24.62 angstroms. LZ-210 zeolites having a silica-to-alumina mole ratio below 20 generally have a sorptive capacity for water vapor at 25° C. and 4.6 mm mercury water vapor partial pressure of at least 20 weight percent based on the anhydrous weight of the zeolite. Normally, the oxygen sorptive capacity at 100 mm mercury and −183° C. will be at least 25 weight percent.

LZ-210 zeolites are resistant to crystal collapse at elevated temperatures. These zeolites are stable in dry air at temperatures of at least 975° C., and are often stable at a temperature of at least 1035° C. This resistance to crystal collapse compares favorably with a typical sodium Y zeolite that is ion-exchanged with ammonium ions and which collapses at a temperature of about 861° C.

In general, LZ-210 zeolites may be prepared by contacting a conventional Y zeolite having an overall silica-to-alumina mole ratio less than about 6.0 with an aqueous solution of a fluorosilicate salt, preferably a solution of ammonium hexafluorosilicate to extract aluminum from the framework structure while incorporating silicon from the solution therein. The dealumination and silicon incorporation is accomplished by placing an ammonium-exchanged Y zeolite into an aqueous reaction medium such as an aqueous solution of ammonium acetate, and slowly adding an aqueous solution of ammonium hexafluorosilicate. After allowing the reaction to proceed, a zeolite having an increased silica-to-alumina mole ratio is produced. The magnitude of the increase is dependent at least in part on the amount of fluorosilicate solution contacted with the zeolite and on the reaction time allowed. Normally, a reaction time of between about 10 and about 24 hours is sufficient for equilibrium t be achieved. The resulting solid product, which may be separated from the aqueous reaction medium by conventional filtration techniques, is a form of LZ-210 zeolite. In order to provide greater activity and crystalline stability, this product may be subjected to a steam calcination by contacting the product with water vapor at a partial pressure of at least 0.2 p.s.i.a. for a period of between about ¼ to about 3 hours at a temperature between about 900° F. and about 1500° F.

At present, it is preferred that the catalyst of the invention contain only the zeolites described above, i.e., zeolite beta and a dealuminated Y zeolite having an overall silica-to-alumina mole ratio above 6.0. Preferably, the catalyst will be devoid of any other zeolites (zeolitic molecular sieve) or nonzeolitic molecular sieves, including those sieves having pores of intermediate or small size, i.e., below 7.0 angstroxs, which are not defined by 12-members rings of oxygen atoms, and sieves having a large pore size such as rare earth-exchanged Y zeolites, ultrastable Y zeolites, ZSM-4 zeolite, ZSM-18 zeolite and ZSM-20 zeolite. However, in alternative but non-preferred embodiments of the invention, other zeolites or nonzeolitic molecular sieve may also be present. The term "molecular sieve" as used herein refers to any material capable of separating atoms or molecules based on their respective dimensions. Molecular sieves include zeolites, microporous carbons, porous membranes, aluminas and the like. The term "pore size" as used herein refers to the diameter of the largest molecule that can be sorbed by the particular molecular sieve in question. The measurement of such diameters and pore sizes is discussed more fully in Chapter 8 of the book entitled *Zeolite Molecular Sieves* written by D. W. Breck and published by John Wiley & Sons in 1974, the disclosure of which book is hereby incorporated by reference in its entirety. The term "nonzeolitic" as used herein refers to molecular sieves whose frameworks are not formed of substantially only silicon and aluminum atoms in tetrahedral coordination with oxygen atoms. "Zeolitic" molecular sieves are distinguished from nonzeolitic molecular sieves in that their frameworks are formed of substantially only silicon and aluminum atoms in tetrahedral coordination with oxygen atoms, such as the frameworks present in ZSM-5 zeolites, Y zeolites and X zeolites.

The stability and/or acidity of either or both of the two zeolites used in the catalyst of the invention may be increased by exchanging the zeolite with ammonium ions, thereby lowering the alkali metal content until it is less than about 0.8 weight percent, preferably less than about 0.5 weight percent, and most preferably less than about 0.3 weight percent, calculated as the monoxide. Methods of carrying out the ion exchange are well known in the art. It is normally preferred that both zeolite components of the catalyst be substantially free of rare earth components. The unit cell size of the dealuminated Y zeolite after it has been calcined in steam and then exchanged with ammonium ions will typically be in the range between about 24.41 and 24.54 angstroms.

The two zeolites required in the catalyst of the invention are embodied into particles which contain both zeolites. In the preferred method, this is accomplished by combining the zeolites with a material, such as an alumina hydrogel, which, upon calcination, will yield a porous, inorganic refractory oxide, or with a material which itself is a porous, inorganic refractory oxide, for example, alumina, silica-alumina, silica-magnesia, and clays such as kaolin, as well as combinations of such materials. Perhaps the most convenient method for physically integrating the two zeolites into individual particulates is to comull a porous, inorganic refractory oxide (e.g., alumina such as Catapal alumina or a Ziegler alumina, or peptized alumina, when the preferred porous refractory oxide desired is alumina) with the two zeolites, and subsequently extruding the comulled material through a die having small openings therein of desired cross-sectional size and shape, e.g., circle, trilobal cloverleaf, quadrolobal cloverleafs, etc., breaking or cutting the extruded matter into appropriate lengths, e.g., ⅛ to ¾ inch, drying the extrudates, and then calcining at a temperature, e.g., 900° F. or higher, to produce a material suitable for use as a catalyst or as a catalyst component for use in high temperature chemical conversion reactions. At present it is preferred that the catalyst be produced in cylindrical form; however, as stated above, other cross-sectional shapes are possible, such as cloverleafs of polylobal design, for example, trilobal or quadrolobal shapes, as shown, for example, in FIGS. 8 and 10, respectively, in U.S. Pat. No. 4,028,227 herein incorporated by reference in its entirety.

It will be understood, of course, in the foregoing description that the porous, inorganic refractory oxide is used as a binder material to hold the zeolites together in the support, and accordingly, if desired, other materials can also be incorporated into the comulled mixture, including for example, other inorganic refractory oxide diluents which may or may not possess some type of catalytic activity, and particulates of porous, inorganic refractory oxides which have already been calcined. Additionally and alternatively, hydrogenation component precursors can also be comulled into the mixture, as will be discussed in more detail hereinafter.

It will be further understood that producing the catalyst of the invention in extrudate form, while certainly the most highly preferred method, is still but one option available to those skilled in the art. The catalyst may also be produced in tablet, granules, spheres, and pellets, as desired, by any known method for combining other zeolites with porous, inorganic refractory oxide component(s).

The catalyst of the invention can be used for converting hydrocarbons and other organic compounds into more valuable reaction products by acid catalyzed reactions, such as alkylation, transalkylation, dealkylation, isomerization, dehydrocyclization, dehydrogenation, hydrogenation, cracking, hydrocracking, dewaxing, hydrodewaxing, oligomerization, aromatization, alcohol conversion reactions, the conversion of syngas into mixtures of hydrocarbons, and the like. When the catalyst contains the two zeolites and a porous, inorganic refractory oxide component but no hydrogenation components, it is useful for any of a number of acid-catalyzed hydrocarbon conversion reactions in which hydrogen is not an added reactant, e.g., isomerization, alkylation, transalkylation, cracking, dewaxing, oligomerization, etc. However, since the main benefit of the invention as presently contemplated is in hydroprocessing such as hydrocracking, a process in which hydrogen is an added reactant, the catalyst for this purpose will further require one or more hydrogenation components, in which case the portion of the catalyst exclusive of any hydrogenation metal components is considered the support upon which the hydrogenation component(s) is dispersed.

Whether the zeolite-refractory oxide particulates are used as the catalyst itself or as the support (or support component) for hydrogenation metals, it is preferred that such zeolite-refractory oxide particulates contain at east 5 weight percent, more preferably at least 10 weight percent, and more preferably still, at least 20 weight percent each of zeolite beta and the dealuminated Y zeolites described above and at least 5 weight percent, more preferably at least 10 weight percent, and more preferably still, at least 15 weight percent of one or more of the amorphous, porous, inorganic refractory oxides. The zeolite-refractory oxide particulates typically contain at least 35 weight percent, preferably at least 50 percent by weight, even more preferably between about 60 and 80 percent by weight, of the two zeolites combined, with at least 50 percent by weight, preferably at least 75 percent by weight, even more preferably at least 90 percent by weight, and most preferably 100 percent by weight of the balance being the one or more porous, inorganic refractory oxides. In a preferred embodiment, the weight ratio of the two zeolites in the catalyst is about 1.67; however, other weight ratios of zeolite beta to the dealuminated Y zeolites described above may also be used, e.g., in the ranges of 0.25 to 4.0, 0.50 to 2.0 and 0.8 to 1.2.

For use in hydroprocessing, such as hydrocracking, the catalyst contains one or more hydrogenation components containing metals selected from Group VIB and/or Group VIII of the Periodic Table of Elements, such components typically being in the form of the free metals or their respective oxides and sulfides, the latter two being most preferred. As used herin "Periodic Table of Elements" refers to the version found in the inside front cover of the *Handbook of Chemistry and Physics*, 65th Edition, published in 1984 by the Chemical Rubber Company, Cleveland, Ohio. The platinum group (or noble) metals of the Group VIII metals may be used, but preference at present is for the base (or non-noble) metals, e.g., nickel and cobalt in particular, and nickel most preferably of all. Of the Group VIB metals, molybdenum and tungsten are preferred, with molybdenum being most preferred. The most highly preferred catalyst contains both a non-noble Group VIII metal component and a Group VIB metal component, most preferably nickel and molybdenum in combination.

The hydrocracking catalysts of the invention contain at least 0.2 weight percent of the hydrogenation components, calculated as the metals. If noble metals are used, the hydrogenation components are generally present in a relatively low proportion, e.g., 0.2 to 2 weight percent. For the base metals, the proportions are generally higher. The Group VIB metal component is generally employed in proportions of about 5 to 35 weight percent, preferably in the range of 8 to 30 weight percent, calculated as the respective trioxide. Non-noble Group VIII metal components are typically employed in proportions between about 1 and 15 weight percent, preferably between 3 and 10 percent by weight, calculated as the respective monoxide. It is to be understood that the proportions given above for the hydrogenation metal components are based on the finished catalyst whereas the proportions expressed above for the zeolites and amorphous inorganic refractory oxides are values in the absence of the hydrogenation metal component, i.e., for the support only. For purposes herein, the term "support" is defined as all materials in the catalyst except the hydrogenation metal components.

The hydrogenation components may be incorporated into the catalyst in any of many ways known in the art for combining hydrogenation components with supports composed of zeolites and refractory oxides. One such method is to first prepare the support, for example, as an extrudate, containing the zeolites and refractory oxide in calcined form, and then impregnating the support with solutions containing the desired metal(s) in dissolved form. Calcination at an elevated temperature, e.g., above 800° F., produces the desired catalyst containing metals in oxide form. Likewise, and in the preferred embodiment, the desired metal(s) are introduced by comulling a compound containing such metal(s) in the zeolite-refractory oxide mixture previously described, followed by shaping (e.g., extrusion through a die), drying, and calcining. e.g., at a temperature above 900° F., to produce the oxide form of the catalyst. For the preferred catalyst, the comulling is effected with ammonium heptamolybdate as the source of molybdenum and nickel nitrate as the source of nickel, with both compounds generally being introduced into the mulling mixture in the form of an aqueous solution. Other metals can be similarly introduced in dissolved aqueous form; likewise, non-metallic elements, e.g., phosphorus, may be introduced by incorporating a soluble component such as phosphoric acid into the aqueous solution.

It will be noted in the above impregnation and comulling procedures that the final catalyst will inherently contain the hydrogenation metal distributed on the zeolite beta, the dealuminated Y zeolite and the refractory oxide and, in either procedure, if the metal is introduced in dissolved form as a cation, some of the metal will exchange into the cation sites of the two zeolites. However, it is possible, in embodiments of the invention which are not presently preferred, that the hydrogenation metal(s) could be essentially selectively located on either of the zeolites or on both to the exclusion of the refractory oxide, or on the refractory oxide to the exclusion of the zeolites, or on one zeolite and the refractory oxide to the exclusion of the other zeolite. As an example, one could introduce the hydrogenation metal by cation exchange into the zeolites or by impregnation thereon if the metal is present in anionic form; subsequent comulling with the porous, inorganic refractory oxide, followed by shaping, drying, and calcining, would ultimately yield a catalyst containing the hydrogenation metals only on the zeolites. In direct contrast, one could comull the hydrogenation metal precursor with only the porous refractory oxide, and then add the zeolites to the comulling mixture; subsequent shaping, drying, and calcining steps yield a catalyst with the hydrogenation metal essentially exclusively on the porous, inorganic refractory oxide. Alternatively still, one could cation exchange and/or impregnate one of the zeolites with the desired metals, and likewise separately comull the metals with the porous, inorganic refractory oxide, then comull the entire combination, shape, dry, and calcine as before but this time yielding a catalyst having the hydrogenation metals on one zeolite and on the porous refractory oxide to the exclusion of the second zeolite. In addition, the preceding procedure can be modified such that no metals are comulled into the refractory oxide, thus providing a catalyst in which the hydrogenation component is essentially exclusively on one or the other of the two zeolites.

By the foregoing procedures or their equivalents, catalysts with the hydrogenation metals present in the oxide form are prepared in particulate form, with the majority of such particles, usually at least 90 percent, and preferably substantially all, individually containing both zeolites and one or more refractory oxides in a support for the hydrogenation component. The finished hydrocracking catalyst will typically comprise (1) between about 5 and 75 weight percent zeolite beta, preferably between about 15 and 50 weight percent, (2) between about 5 and 75 weight percent dealuminated Y zeolite, preferably between about 15 and 50 weight percent, (3) between about 5 and 25 weight percent porous, inorganic refractory oxide, preferably between about 10 and 20 weight percent, (4) between about 8 and 30 weight percent Group VIB metal hydrogenation component, preferably between about 10 and 25 weight percent and (5) between about 0.2 and 15 weight percent Group VIII hydrogenation metal component, preferably between about 0.5 and 10 weight percent.

Catalysts prepared in the oxide form as described above are generally converted to the sulfide form for hydrocracking purposes. This can be accomplished by presulfiding the catalyst prior to use at an elevated temperature, e.g., 300° to 700° F., with, for example, a mixture consisting of 10 volume percent $H_2S$ and 90 volume percent $H_2$. Alternatively, the catalyst can be presulfided ex situ by various sulfiding processes; as an illustration, see "Sulficat: Offsite Presulfiding of Hydroprocessing Catalysts from Eurecat" by J. H. Wilson and G. Berrebi, Catalysis 87, Studies in Surface Science and Catalysis, #38, page 393. The sulfiding can also be accomplished in situ, i.e., by using the catalyst in the oxide form to hydrocrack a hydrocarbon feedstock containing sulfur compounds under hydrocracking conditions, including elevated temperature and pressure and the presence of hydrogen.

Hydrocracking catalysts in accordance with the invention are useful in the conversion of a wide variety of hydrocarbon feedstocks to a hydrocarbon product of lower average boiling point and/or molecular weight. The feedstocks that may be subjected to hydrocracking by the method of the invention include all mineral oils and synthetic oils (e.g., shale oil, tar sand products, etc.) and fractions thereof. Illustrative feedstocks include straight run gas oils, vacuum gas oils, coker gas oils, and catcracker distillates. The typical hydrocracking feedstock, however, contains a substantial proportion of components, usually at least 50 percent by volume, often at least 75 percent by volume, boiling above the desired end point of the product, which end point, in the case of gasoline, will generally be in the range of about 380° to 420° F. Usually, the feedstock will also contain gas oil components boiling above 550° F., with highly useful results being achievable with feeds containing at least 30% by volume of components boiling between 600° and 1100° F.

For best results in hydrocracking, the catalyst of the invention will be employed as a fixed bed of catalytic particulates in a hydrocracking reactor vessel into which hydrogen and the feedstock are introduced and passed in a downwardly direction. Operating conditions in the reactor vessel are chosen so as to convert the feedstock into the desired product, which, in the preferred embodiment, is a hydrocarbon product containing a substantial proportion of gasoline components boiling, for example, in the 185° to 420° F. range. However, other products, such as turbine fuel or diesel fuel, may also be desired on occasion, and conditions must be adjusted according to the product (or distribution of products) desired. The exact conditions required in a given situation will depend upon the nature of the feedstock, the particular catalyst composition utilized, and the desired product(s). In general, the conditions of operation for hydrocracking will fall into the following usual and preferred ranges:

TABLE 2

| Conditions | Usual | Preferred |
|---|---|---|
| Temperature. | | |
| °F. | 450–850 | 500–800 |
| °C. | 232–454 | 260–427 |
| Pressure. | | |
| psig | 750–3500 | 1000–3000 |
| atm | 51–238 | 68–204 |
| LHSV, reciprocal hours | 0.3–5.0 | 0.5–3.0 |
| $H_2$/Feedstock, MSCF/bbl as measured at 60° F. (15.6° C.) and 1 atmosphere | 1–10 | 2–8 |

The foregoing Table 2 shows the suitable and preferred hydrocracking conditions for single stage or for each stage of a two stage operation (the latter being described more fully in U.S. Pat. No. 4,429,053). It will be understood, however, that the operating conditions in the two stages of the two stage process are not necessarily identical. In fact, as mentioned hereinbefore, the primary difference in conditions in the two hydrocracking reactor vessels of two stage operation is the presence of substantial ammonia, usually greater than about 2,000 ppmv or higher in the first stage and its essential absence, i.e. less than 200 ppmv and preferably less than about 20 ppmv, in the second, allowing for less severe conditions in the second stage. There may, however, be yet other differences in conditions in any particular situation.

Based on presently available data, the catalyst of the present invention as compared to a commercial gasoline hydrocracking catalyst containing a single steam-stabilized Y zeolite having an overall silica-to-alumina mole ratio less than 6.0 provides for enhanced results when used for single stage operation or in either stage of the two stage process. In particular, the catalyst of the invention provides for much higher activity in both stages of the two stage process, a significant increase in the yield of gasoline boiling in the 185° to 420° F. range in the second stage of the two stage process and greater yields of gasoline boiling in the 50° to 420° F. range in both first and second stages. These achievements, and others, are proven in the following comparative example, which is provided for illustrative purposes and not to limit the invention as defined by the claims.

COMPARATIVE EXAMPLE

Catalyst 1

Catalyst 1 was prepared by comulling a mixture of 64 wt. % zeolite beta having a silica-to-alumina mole ratio of about 26, 16 wt. % peptized Catapal alumina, sufficient nickel nitrate to provide 5 wt. % nickel (calculated as NiO) in the final catalyst and sufficient ammonium heptamolybdate to provide 15 wt. % molybdenum (calculated as $MoO_3$) in the final catalyst. The comulled mixture was then extruded into 1/16 inch diameter cylindrical particles of between ⅛ and ½ inch in length, dried and calcined at 900° F. The resulting catalyst contained the nickel and molybdenum in the proportions above specified on a support comprising 80 weight percent zeolite beta and 20 weight percent alumina.

Catalyst 2

Catalyst 2, a catalyst of the invention, was prepared by comulling a mixture of 24 wt. % of the zeolite beta used in Catalyst 1, 40 wt. % of a steamed and ammonium-exchanged LZ-210 zeolite having an overall silicato-alumina mole ratio of 12 and a unit cell size of 24.41 angstroms, 16 wt. % peptized Catapal alumina, sufficient nickel nitrate to provide 5 wt. % nickel (calculated as NiO) in the final catalyst and sufficient ammonium heptamolybdate to provide 15 wt. % molybdenum (calculated as $MoO_3$) in the final catalyst. The comulled mixture was then extruded into 1/16 inch diameter cylindrical particles of between ⅛ and ½ inch in length, dried and calcined at 900° F. The resulting catalyst contained the nickel and molybdenum in the proportions above specified on a support comprising 30 weight percent zeolite beta, 50 weight percent LZ-210 zeolite, and 20 weight percent alumina.

Catalyst 3

Catalyst 3 was prepared similarly to Catalyst 2 except that 40 wt. % LZ-10 zeolite having a unit cell size of about 24.30 angstroms, a pore size greater than 7.0 angstroms and an overall silica-to-alumina mole ratio of 5.2 was used in place of the steamed and ammonium exchanged LZ-210 zeolite. LZ-10 is an ultrahydrophobic Y (UHP-Y) zeolite whose composition and properties are disclosed in U.S. Pat. Nos. 4,401,556 and 4,419,271, the disclosures of which are both incorporated herein by reference in their entireties. The resulting catalyst contained the nickel and molybdenum in the proportions above specified for Catalyst 2 on a support comprising 30 weight percent zeolite beta, 50 weight percent LZ-10 zeolite, and 20 weight percent alumina.

Catalyst 4

Catalyst 4, which is a sample of a commercially available gasoline hydrocracking catalyst, was prepared similarly to Catalyst 1 except that 64 wt. % LZY-82 zeolite having a unit cell size of about 24.55 angstroms and an overall silica-to-alumina mole ratio of 5.7 was used in place of the zeolite beta. LZY-82 zeolite is a large pore steam-stabilized Y zeolite prepared as described in U.S. Pat. No. 3,929,672. The resulting catalyst contained the nickel and molybdenum in the proportions above specified for Catalyst 1 on a support comprising 80 weight percent LZY-82 zeolite and 20 weight percent alumina.

Each of the four catalysts was presulfided by passing a gas stream consisting of 10 vol. % $H_2S$ and the balance $H_2$ through a bed of the catalyst at a temperature initially of about 300° F. and slowly increased to 700° F. and held at that temperature for about 1 hour.

The four catalysts were compared for hydrocracking activity and selectivity (i.e., product yields) in both simulated first and second stage testing. Specifically, the four catalysts were separately tested for hydrocracking a hydrotreated, partially hydrocracked vacuum gas oil feed having an API gravity of 38.7°, an initial boiling point of 373° F., a final boiling point of 807° F., and a 50% boiling point of 568° F., with about 8 vol. % boiling below 400° F., as determined by a modified ASTM D1160 distillation.

Each catalyst was first tested for simulated second stage operation in the substantial absence of ammonia by passing the feedstock through a laboratory size reactor vessel containing 150 milliliters of the catalyst at a total pressure of 1450 psig, a space velocity of 1.7 LHSV, and a hydrogen feed rate of 8000 standard cubic feet per barrel of feed as measured at 60° F. In addition, sufficient thiophene was added to the feed to provide a hydrogen sulfide concentration equivalent to 0.5 weight percent sulfur and thereby simulate a hydrogen sulfide-containing atmosphere as it exists in commercial second stage hydrocracking reactors. The temperature conditions were adjusted as necessary to maintain a product of 49.5° API gravity, which, by previously established correlations, corresponds to about a 60 volume percent yield of gasoline-type materials boiling below 420° F., over the course of 100 hours. At the end of the 100 hours, the temperature required to maintain the product was recorded, and using Catalyst 4 as a reference, the activity and selectivity of each catalyst relative to this catalyst were calculated. These comparative data, and other data relative to the second stage simulation, are summarized in Table 3 below.

After the second stage simulation, the conditions in the reactor vessel were altered for first stage simulation under ammonia-rich conditions, in particular, by adding sufficient tert-butyl amine to the feed to provide an ammonia concentration equivalent to 0.2 weight percent nitrogen and adjusting the temperature to maintain production of a liquid product of 47.0° API gravity, which, by previously established correlations, corresponds to about a 40 percent yield of gasoline-type products boiling below 420° F. Again, after 100 hours operation, data were recorded comparing the catalysts against the performance of Catalyst 4 as a reference, the data being summarized in the following Table 3.

TABLE 3

| | Catalyst Designation: | | | |
|---|---|---|---|---|
| | 1 | 2 | 3 | 4** |
| Composition, wt. % | | | | |
| LZ-10 | — | — | 40 | — |
| LZ-210 | — | 40 | — | — |
| zeolite beta | 64 | 24 | 24 | — |
| LZY-82 | — | — | — | 64 |
| Second Stage: | | | | |
| Activity, °F. | −42 | −41 | −17 | 0 |
| $C_1$-$C_3$ yield, scf/bbl | −8.2 | +3.4 | +15.5 | 0 |
| $C_4$ yield, vol. % | +1.4 | −0.2 | +0.6 | 0 |
| 50–185° F. fraction $C_5$-$C_6$ yield, vol. % | +10.6 | +7.3 | +7.2 | 0 |
| 185–420° F. fraction yield, vol. % | −2.9 | +2.0 | +2.1 | 0 |
| $C_4$–420° F. yield, vol. % | +9.1 | +9.1 | +9.9 | 0 |
| 50–420° F. yield, vol. % | +7.7 | +9.3 | +9.3 | 0 |
| First Stage: | | | | |
| Activity, °F. | −31 | −19 | −2 | 0 |
| $C_1$-$C_3$ yield, scf/bbl | +6.7 | +1.5 | +12.5 | 0 |
| $C_4$ yield, vol. % | +0.5 | −2.3 | −0.8 | 0 |
| 50–185° F. fraction $C_5$-$C_6$ yield, vol. % | +8.1 | +1.3 | +4.2 | 0 |
| 185–420° F. fraction yield, vol. % | −3.6 | +0.6 | +0.4 | 0 |
| $C_4$–420° F. yield, vol. % | +5.0 | −0.4 | +3.8 | 0 |
| 50–420° F. yield, vol. % | +4.5 | +1.9 | +4.6 | 0 |

**Catalyst 4 is used as a reference to evaluate the performance of Catalysts 1 through 3. Thus, the first and second stage activity and yield data for Catalyst 4 are entered as zeroes while the data for Catalysts 1 through 3 are entered as the difference between the actual value for activity or yield of the catalyst minus the actual value for activity or yield obtained with Catalyst 4.

As shown in Table 3, the catalytic activity of Catalyst 2, a catalyst of the invention containing a combination of zeolite beta and a steamed and ammonium-exchanged LZ-210 zeolite having a silica-to-alumina mole ratio of 12, is substantially higher than that of the reference commercial catalyst, i.e., Catalyst 4, in both simulated first and second stage hydrocracking. In addition, Catalyst 2 has significantly higher first and second stage activity compared to Catalyst 3, which is similar to Catalyst 2 but contains LZ-10 zeolite, a hydrothermally treated Y zeolite having a silica-to-alumina mole ratio less than 6.0, in place of LZ-210 zeolite. Catalyst 2 is 17°

F. [-19-(-2)] more active than Catalyst 3 in the first stage and 24° F. [-41-(-17)] more active in the second stage. A comparison of the catalyst of the invention to Catalyst 1, which contains zeolite beta and no other zeolite, shows that the second stage activities are about equal but that Catalyst 1 is 12° F. [-31-(-19)] more active for first stage hydrocracking in the presence of ammonia. Although Catalyst 1 shows an activity advantage over the catalyst of the invention in first stage hydrocracking, the differential in yield of heavy gasoline, i.e. the 185°-420° F. boiling fraction, obtained with the catalyst of the invention in both the first (+4.2 volume percent) and second stages (+4.9 volume percent) is significant enough to counterbalance any activity advantage. Increased yields of heavy gasoline are desirable since such a product is used as a reformer feedstock to produce high octane gasoline blending stock which has a relatively low vapor pressure that makes it highly desirable for use in making environmentally acceptable gasolines. The heavy gasoline is also an excellent feedstock for producing petrochemicals.

A comparison of product yields obtained with the catalyst of the invention, Catalyst 2, to yields obtained with the commercial catalyst, Catalyst 4, indicate a significant advantage in yield in both light gasoline, the 50°-185° F. boiling fraction, and heavy gasoline, the 185°-420° F. boiling fraction, in second stage hydrocracking. The catalyst of the invention yields 7.3 volume percent more light and 2.0 volume percent more heavy gasoline. Catalyst 2 also shows a small advantage in yields of these components in first stage hydrocracking. Although the yields of light and heavy gasoline obtained with Catalyst 3 are similar to those obtained with Catalyst 2 in both stages, the activity advantage shown by Catalyst 2 makes it a far superior catalyst.

In summary, as to the data in Table 3, it has been found that Catalyst 2 containing a mixture of zeolite beta and a steamed and ammonium-exchanged LZ-210 zeolite having an overall silica-to-alumina mole ratio of 12 is superior in activity and in selectivity for producing light and heavy gasoline in both first or second stage hydrocracking to a current commercial catalyst (Catalyst 4) containing Y-82 zeolite as the only zeolite therein. In addition, Catalyst 2 is unexpectedly superior to Catalyst 3 containing zeolite beta in combination with LZ-10 zeolite, a hydrothermally modified Y zeolite having a silica-to-alumina mole ratio less than 6.0, for activity in both first and second stage hydrocracking.

As shown by the data in Table 3, the catalyst of the invention is most especially effective when one desires 185° to 420° F. gasoline as the main or predominant product. The typical gas oil feedstock contains no more than about 15 volume percent, usually less than 10 volume percent of constituents boiling in the 185° to 420° F. range. When gasoline is the desired product from such feeds, the hydrocracking operating conditions are selected to produce at least a 35 vol. % yield, preferably at least a 45 vol. % yield, even more preferably at least a 50 vol. % yield, and most preferably of all at least a 65 vol. % yield of 185° to 420° F. gasoline product.

Although the invention has been described in conjunction with a comparative example and by reference to a preferred embodiment thereof, it is evident that many alternatives, modifications, and variations will be apparent to those skilled in the art in light of the foregoing description. Accordingly, it is intended in the invention to embrace these and all such alternatives, variations, and modifications as may fall within the spirit and scope of the appended claims.

I claim:

1. A process for hydrocracking a hydrocarbon feedstock which comprises contacting said feedstock at a temperature between about 450° F. and about 850° F. and at a pressure between about 750 psig and about 3500 psig in the presence of hydrogen and in an atmosphere containing no more than about 200 ppmv ammonia with a catalyst comprising a hydrogenation component, zeolite Beta, and between about 15 and about 50 weight percent of a catalytically active dealuminated Y zeolite having a unit cell size between 24.40 and 24.63 angstroms, a sorptive capacity for water vapor at 25° C. and 4.6 millimeters mercury water vapor partial pressure of at least about 20 weight percent, and an overall silica-to-alumina mole ratio greater than 6.0, wherein said dealuminated Y zeolite has (a) a composition expressed in terms of oxide mole ratios in the anhydrous state of

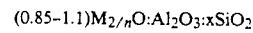

$$(0.85-1.1)M_{2/n}O:Al_2O_3:xSiO_2$$

wherein "M" is a cation having a valence of "n" and "x" has a value between 6 and about 20, (b) an X-ray powder diffraction pattern comprising at least the d-spacings set forth in Table 1 and (c) extraneous silicon atoms in the crystal lattice in the form of framework $SiO_4$ tetrahedra.

2. A process as defined by claim 1 wherein said dealuminated Y zeolite is prepared by contacting a zeolite of the Y crystal structure and an overall silica-to-alumina mole ratio below 6.0 with an aqueous solution of a fluorosilicate salt.

3. A process as defined by claim 2 wherein said fluorosilicate salt is ammonium hexafluorosilicate.

4. A process as defined by claim 3 wherein said zeolite of the Y crystal structure is an ammonium-exchanged Y zeolite.

5. A process as defined by claim 1 wherein "x" has a value between about 8 and 15.

6. A process as defined by claim 5 carried out in a atmosphere which contains no more than about 20 ppmv ammonia.

7. A process as defined by claim 5 carried out in an atmosphere which contains no more than about 20 ppmv ammonia.

8. A process as defined by claim 1 wherein said dealuminated Y zeolite is an LZ-210 zeolite.

9. A process as defined by claim 8 carried out in a atmosphere which contains no more than about 20 ppmv ammonia.

10. A process as defined by claim 1 carried out in a atmosphere which contains no more than about 20 ppmv ammonia.

11. A process as defined by claim 1 wherein "x" has a value between about 9 and about 13.

12. A process as defined by claim 11 carried out in an atmosphere which contains no more than about 20 ppmv ammonia.

13. A hydrocracking process which comprises contacting a hydrocarbon feedstock with a hydrocracking catalyst in the presence of added hydrogen at a temperature between about 450° F. and about 850° F. and at a pressure between about 750 psig and about 3500 psig in an atmosphere which contains no more than about 200 ppmv ammonia, wherein said catalyst comprises one or more hydrogenation components in combination with a support comprising an amorphous, inorganic refractory oxide binder, zeolite Beta in a form catalytically active for cracking hydrocarbons, and a dealuminated Y zeolite in a form catalytically active for cracking hydrocarbons, wherein said dealuminated Y zeolite (a) has an overall silica-to-alumina mole ratio greater than 6.0, a unit cell size between 24.40 and 24.63 angstroms and a sorptive capacity for water vapor at 25° C. and 4.6 millimeters mercury water vapor partial pressure of at least about 20 weight percent, (b) is present in said catalyst in an amount between about 15 and about 50 weight percent of said catalyst, (c) has a composition expressed in terms of oxide mole ratios in the anhydrous state of $$(0.85-1.1)M_{2/n}O:Al_2O_3:xSiO_2$$

wherein "M" is a cation having a valence of "n" and "x" has a value between 6 and about 20, (d) has an X-ray powder diffraction pattern comprising at least the d-spacings set forth in Table 1 and (e) has extraneous silicon atoms in the crystal lattice in the form of framework $SiO_4$ tetrahedra.

14. A hydrocracking process as defined by claim 13 wherein said support comprises at least 10 weight percent of each zeolite.

15. A hydrocracking process as defined by claim 14 wherein said porous, inorganic refractory oxide binder comprises alumina and said alumina comprises at least 10 weight percent of said support.

16. A hydrocracking process as defined by claim 15 wherein said hydrogenation components comprise a metal selected from the group consisting of Group VIB metals and Group VIII metals.

17. A hydrocracking process as defined by claim 16 wherein said support comprises at least 20 weight percent of each zeolite.

18. A hydrocracking process as defined by claim 17 wherein said catalyst comprises both a Group VIB metal hydrogenation component and a Group VIII non-noble metal hydrogenation component.

19. A hydrocracking process as defined by claim 18 wherein said dealuminated Y zeolite is produced by contacting a zeolite of the Y crystal structure having a silica-to-alumina mole ratio below 6.0 with an aqueous solution of a fluorosilicate salt.

20. A hydrocracking process as defined by claim 19 wherein said zeolite of the Y crystal structure comprises an ammonium-exchanged zeolite and said fluorosilicate salt is ammonium hexafluorosilicate.

21. A hydrocracking process as defined by claim 18 wherein the product comprises greater than about 35 volume percent gasoline boiling in the range between 185° F. and 420° F. and said feedstock contains no more than about 15 volume percent of gasoline boiling in said range.

22. A hydrocracking process as defined by claim 18 wherein said Group VIB metal hydrogenation component comprises a metal selected from the group consisting of molybdenum and tungsten and said Group VIII non-noble metal hydrogenation component comprises a metal selected from the group consisting of nickel and cobalt.

23. A hydrocracking process as defined by claim 22 carried out in an atmosphere which contains no more than about 20 ppmv ammonia.

24. A hydrocracking process as defined by claim 22 wherein said support comprises said zeolite beta and said dealuminated Y zeolite in a combined concentration of at least about 45 weight percent.

25. A hydrocracking process as defined by claim 24 wherein said zeolite beta and said dealuminated Y zeolite are present in said catalyst in a weight ratio of zeolite beta to dealuminated Y zeolite between about 0.5 and 2.

26. A hydrocracking process as defined by claim 25 wherein said Group VIB metal hydrogenation component comprises molybdenum and said Group VIII metal hydrogenation component comprises nickel.

27. A hydrocracking process as defined by claim 26 wherein said catalyst comprises between about 10 and 30 weight percent of said molybdenum component, calculated as $MoO_3$, and between about 3 and 10 weight percent of said nickel component, calculated as NiO.

28. A hydrocracking process as defined by claim 26 carried out in an atmosphere which contains no more than about 20 ppmv ammonia.

29. A hydrocracking process as defined by claim 13 carried out in an atmosphere which contains no more than about 20 ppmv ammonia.

30. A hydrocracking process as defined by claim 13 wherein said catalyst is substantially devoid of noble metals.

31. A hydrocracking process as defined by claim 13 wherein "x" has a value between about 8 and about 15.

32. A hydrocracking process as defined by claim 13 wherein "x" has a value between about 9 and about 13.

33. A hydrocracking process for producing gasoline which comprises contacting a gas oil feedstock with a hydrocracking catalyst in the presence of added hydrogen at a temperature between about 450° F. and about 850° F. and at a pressure between about 750 psig and about 3500 psig in an atmosphere which contains no more than about 200 mmpv ammonia, wherein said catalyst comprises:

(a) a hydrogenation component comprising a metal selected from Group VIB and/or Group VIII of the Periodic Table of Elements;

(b) zeolite Beta in a form catalytically active for cracking hydrocarbons;

(c) between about 15 and 50 weight percent of an LZ-210 zeolite having a silica-to-alumina mole ratio between 6 and about 15 in a form catalytically active for cracking hydrocarbons; and (d) an amorphous, inorganic refractory oxide binder.

34. A hydrocracking process as defined by claim 32 wherein said catalyst contains a hydrogenation component comprising a Group VIB metal and a hydrogenation component comprising a Group VIII non-noble metal.

35. A hydrocracking process as defined by claim 34 wherein said Group VIB metal is molybdenum and said Group VIII metal is nickel.

36. A hydrocracking process as defined by claim 34 carried out in an atmosphere which contains no more than about 20 ppmv ammonia.

37. A hydrocracking process as defined by claim 35 wherein said LZ-210 zeolite has a silica-to-alumina mole ratio from about 9 to 13.

38. A hydrocracking process as defined by claim 37 wherein the product comprises greater than about 40 volume percent gasoline boiling in the range between 180° F. and 420° F., and said gas oil feedstock contains no more than about 10 volume percent of gasoline boiling in said range.

39. A hydrocracking process as defined by claim 37 carried out in an atmosphere which contains no more that about 20 ppmv ammonia.

40. A hydrocracking process as defined by claim 33 wherein said catalyst further comprises an inorganic refractory oxide diluent.

41. A hydrocracking process as defined by claim 33 wherein said catalyst comprises between about 5 and about 75 weight percent of said zeolite beta, between about 15 and about 50 weight percent of said LZ-210 zeolite, between about 5 and about 25 weight percent of said refractory oxide binder, between about 8 and about 30 weight percent of said Group VIB metal component, calculated as the trioxide, and between about 0.2 and about 15 weight percent of said Group VIII metal component calculated as the monoxide.

42. A hydrocracking process as defined by claim 33 wherein said refractory oxide binder is alumina.

43. A hydrocracking process as defined by claim 42 carried out in an atmosphere which contains no more than about 20 ppmv ammonia.

44. A hydrocracking process as defined by claim 33 wherein said catalyst is devoid of a molecular sieve having a pore size below 7.0 angstroms.

45. A hydrocracking process as defined by claim 33 wherein said catalyst is devoid of rare earth metals.

46. A hydrocracking process as defined by claim 33 wherein said catalyst is devoid of an ultrastable Y zeolite, a rare earth-exchanged Y zeolite, ZSM-4 zeolite, ZSM-18 zeolite and ZSM-20 zeolite.

* * * * *

UNITED STATES PATENT AND TRADEMARK OFFICE
CERTIFICATE OF CORRECTION

PATENT NO. : 5,275,720
DATED : January 4, 1994
INVENTOR(S) : John W. Ward

It is certified that error appears in the above-identified patent and that said Letters Patent is hereby corrected as shown below:

Column 14, Table 3, line 37, under column titled "Catalyst Designation 1," replace "8.2" with -- 8.3 --.

Column 18, claim 33, line 37, after "200" replace "mmpv" with -- ppmv --.

Signed and Sealed this

Twenty-sixth Day of July, 1994

Attest:

BRUCE LEHMAN

*Attesting Officer*    Commissioner of Patents and Trademarks